(12) United States Patent
Ivinson et al.

(10) Patent No.: US 9,868,194 B2
(45) Date of Patent: Jan. 16, 2018

(54) REVERSIBLE MULTIPLE USE DISPOSABLE TORQUE LIMITING DEVICE

(71) Applicant: ECA Medical Instruments, Newbury Park, CA (US)

(72) Inventors: David Ivinson, Camarillo, CA (US); John Nino, Simi Valley, CA (US); Gary Norsworthy, Reseda, CA (US)

(73) Assignee: ECA Medical Instruments, Newbury Park, CA (US)

( * ) Notice: Subject to any disclaimer, the term of this patent is extended or adjusted under 35 U.S.C. 154(b) by 140 days.

(21) Appl. No.: 15/065,722

(22) Filed: Mar. 9, 2016

(65) Prior Publication Data

US 2016/0184043 A1     Jun. 30, 2016

Related U.S. Application Data

(63) Continuation-in-part of application No. 14/290,674, filed on May 29, 2014, now abandoned, which is a
(Continued)

(51) Int. Cl.
     *A61B 19/00*          (2006.01)
     *B25B 15/02*          (2006.01)
     (Continued)

(52) U.S. Cl.
     CPC .......... *B25B 15/02* (2013.01); *B25B 23/1427* (2013.01); *F16D 7/046* (2013.01);
     (Continued)

(58) Field of Classification Search
CPC ... A61B 19/30; A61B 2019/301; A61B 19/00; A61B 2090/031; A61B 90/03; A61B 2017/0023; A61B 2017/0046; A61B 2017/00871; B25B 23/141; B25B 23/1415; B25B 23/1427; B25B 15/02; A61C 3/00; Y10T 29/49826; F16D 43/2026; F16D 7/046; F16D 9/06
See application file for complete search history.

(56) References Cited

U.S. PATENT DOCUMENTS 2,561,136 A * 7/1951 Richardson ............. F16D 7/044
                                                     464/39
3,535,958 A * 10/1970 Larson ................ B25B 23/1427
                                                     81/475

(Continued)

FOREIGN PATENT DOCUMENTS

JP        S59-163466 U      11/1984
JP        61-071375 A       4/1986
(Continued)

OTHER PUBLICATIONS

International Search Report dated Feb. 21, 2013; issued in PCT/US2012/066234.
(Continued)

*Primary Examiner* — Marc Carlson
(74) *Attorney, Agent, or Firm* — Baker & Hostetler LLP

(57) ABSTRACT

A torque limiting device is disclosed, comprising a hollow body with an open proximal end and open distal end forming a handle, an internal wall bisecting said hollow body into a first and a second section on one side having torque limiting movable ramps, a rotatable head section affixed movably to the internal wall with bumps extended from the backside thereof, and a tool mounted to the front side whereby when rotated in a torque limiting direction, the at least one bump stop will pass over the ramp and the application of sufficient torque requirement of said device will depress the ramp, and allow the bump stop to pass over.

12 Claims, 6 Drawing Sheets

Related U.S. Application Data continuation of application No. PCT/US2012/066234, filed on Nov. 21, 2012, application No. 15/065,722, which is a continuation-in-part of application No. 14/007,912, filed on Sep. 26, 2013, now Pat. No. 9,504,528, which is a continuation of application No. PCT/US2012/066090, filed on Nov. 20, 2012.

(60) Provisional application No. 61/565,422, filed on Nov. 30, 2011, provisional application No. 61/610,405, filed on Mar. 13, 2012.

(51) Int. Cl.
| | | |
|---|---|---|
| *B25B 23/142* | (2006.01) | |
| *F16D 9/06* | (2006.01) | |
| *F16D 7/04* | (2006.01) | |
| *F16D 43/202* | (2006.01) | |
| *A61B 17/00* | (2006.01) | |
| *A61B 90/00* | (2016.01) | |

(52) U.S. Cl.
CPC ........... *F16D 9/06* (2013.01); *F16D 43/2026* (2013.01); *A61B 2017/0023* (2013.01); *A61B 2017/0046* (2013.01); *A61B 2017/00871* (2013.01); *A61B 2090/031* (2016.02)

(56) References Cited

U.S. PATENT DOCUMENTS

| | | |
|---|---|---|
| 3,640,141 A | 2/1972 | Hollingsead et al. |
| 6,439,086 B1 | 8/2002 | Bahr |
| 7,938,046 B2 | 5/2011 | Nino et al. |
| 7,992,472 B2 | 8/2011 | Gao |
| 8,276,487 B2 | 10/2012 | Wengreen et al. |
| 2009/0255386 A1* | 10/2009 | Liao ........................ B25B 13/06 81/474 |
| 2010/0275744 A1 | 11/2010 | Wengreen et al. |
| 2011/0000347 A1 | 1/2011 | Stark |
| 2011/0056341 A1* | 3/2011 | Lai ........................ B25B 13/06 81/475 |
| 2011/0094354 A1* | 4/2011 | Lai ........................ B25B 13/06 81/475 |
| 2012/0227221 A1* | 9/2012 | Whitaker ........... A61M 39/1011 24/459 |
| 2014/0366691 A1* | 12/2014 | Ivinson ................ B25B 23/141 81/475 |
| 2015/0202018 A1 | 7/2015 | Schaller et al. |
| 2015/0342693 A1* | 12/2015 | Ivinson .................... F16D 7/04 464/38 |

FOREIGN PATENT DOCUMENTS

| | | |
|---|---|---|
| JP | 2001-121444 A | 5/2001 |
| KR | 10-1999-0074689 | 10/1999 |
| WO | WO 2011/139902 A2 | 11/2011 |
| WO | WO 2013/081934 A1 | 6/2013 |
| WO | WO 2013081934 A1 * | 6/2013 ........... A61C 8/0089 |

OTHER PUBLICATIONS

The Skinny on Living Hinges; Dec. 2010 Design Tips; retrieved on Jul. 15, 2015; Retrieved from the internet <URL http://www.protolabs.com>.

International Patent Application No. PCT/US2012/066090; Int'l Search Report and the Written Opinion; dated Mar. 27, 2013; 9 pages.

* cited by examiner

REVERSIBLE MULTIPLE USE DISPOSABLE TORQUE LIMITING DEVICE

CROSS-REFERENCE TO RELATED APPLICATIONS

This application is a continuation-in-part of U.S. patent application Ser. No. 14/290,674 filed May 29, 2014 which is a Continuation of PCT/US2012/066234 filed Nov. 21, 2012, which claims benefit of, and priority to, U.S. provisional application No. 61/565,422, filed Nov. 30, 2011; and is a continuation-in-part of U.S. patent application Ser. No. 14/007,912 filed Sep. 26, 2013, which is a Continuation of PCT/US2012/066090 filed Nov. 20, 2012, which claims benefit of, and priority to, U.S. provisional application No. 61/610,405, filed Mar. 13, 2012, the contents of which are incorporated by this reference, as if fully set forth herein.

1. Field

This disclosure relates to a medical use driver tool and, in particular, to a torque-limiting driver that disengages at a predefined torque limit which provides one use only and has fixed reverse.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely.

Disposable drivers are an easy to use and reliable alternative to the reusable drivers. Typically, each implant, for example, is packaged with a disposable driver designed to the implant's specifications. Once the driver has been used, it can be discarded. Thus, a surgeon can have complete confidence that the disposable driver, packaged with an implant, will impart the precise amount of torque.

DESCRIPTION

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (N m). The joule, which is the SI unit for energy or work, is also defined as an N m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A low cost, limited use, torque limiting driver that will provide a series of torque limited tightenings.

In some exemplary implementations the actuation to be in the clockwise direction and have a torque setting of 15.0+3.0/−2.0 oz-in under no axial load. Maximum torque must remain under 20.0 oz-in under a measured axial load up to 5.0 lbs.

In some exemplary implementations the actuation to be in the clockwise direction and have a torque setting of 15.0+3.0/−2.0 oz-in under no axial load. Maximum torque must remain under 20.0 oz-in under a measured axial load up to 5.0 lbs and there is about 15.0 degrees of minimum free play.

In some exemplary implementations the actuation to be in the clockwise direction and have a torque setting of 15.0+3.0/−2.0 oz-in under no axial load. Maximum torque must remain under 20.0 oz-in under a measured axial load up to 5.0 lbs and there is positive actuation in counterclockwise direction after clockwise torque actuation.

In some exemplary implementations the actuation to be in the clockwise direction and have a torque setting of about 15.0+3.0/−2.0 oz-in under no axial load. Maximum torque must remain under about 20.0 oz-in under a measured axial load up to 5.0 lbs with 15.0 degrees of minimum free play and fixed positive actuation in counterclockwise direction after clockwise torque actuation.

In some exemplary implementations molded flaps forming living hinges provide torque specific features. Said flaps are also referred to as ramps The ramps create torque as the handle turns a nose (movably fixed into a handle) with a tool mounted on a front side end supporting a tool and one or more bump stops on a backside provided to engage and slide over said ramps in a clockwise direction and flat jams to provide stops against a leading edge of said ramps in a counterclockwise rotation. Said stop is not torque limiting but can be used to reverse spin said nose and tool.

In some instances said nose may be molded in a plastic that has better lubricity properties and the device will meet the about 15.0-degree minimum free play requirement. Torque limiting driver is disposed after a maximum of four torque actuations.

In some instances a multiple use torque limiting driver is disclosed, said driver having a hollow body with and open proximal end and open distal end forming a handle; an internal wall bisecting said hollow body into a first and a second section on one side having a torque limiting movable ramps, each with a leading edge; a channel formed through said internal wall fluidly connecting said first and said second sections; a head surrounded by an annular wall which fits movably into said hollow body said head having a front side with a nose extended therefrom which has a tool mounted therein; said head having a backside which fits over said ramps further comprising at least one bump stop with a flat jam; a peg extended therefrom having a catch; a plug with an extended latch of a size and shape to fit through said channel and mates with said peg's catch holding said head to said internal wall; whereby when rotated in a torque limiting direction the at least one bump stop will pass over said ramp the application of sufficient torque to meet the torque requirement of said device and in the reverse direction said flat jam will abut said leading edge and upon rotation will reverse the direction of the tool affixed to the nose.

In some instances, a method of applying torque at a preset limit is disclosed wherein within a handle one or more living hinge movable ramps are formed on an internal wall, said ramps extend upward from the internal wall, the internal wall having a mounting guide there through whereby a support head may be rotatably affixed; the support head having one or more bump stops on a back side that against the internal wall and movable ramps; the bump stops being lined up with the movable ramps whereby rotating the head moves the bumps stops over the movable ramps; the head being connected to a tool extending from a front side of the head; whereby attaching the tool to a fixture or fastener and turning the handle causes the head to rotate and move the bumps over the movable ramps to temporally displace said living hinge, thereby setting a torque limit.

In some instances, a method of applying torque at a preset limit is disclosed wherein within a handle one or more frangible movable ramps are formed on an internal wall, said ramps extend upward from the internal wall, the internal wall having a mounting guide there through whereby a support head may be rotatably affixed; the support head having one or more bump stops on a back side that against the internal wall and movable ramps; the bump stops being lined up with the movable ramps whereby rotating the head moves the bumps stops over the movable ramps; the head being connected to a tool extending from a front side of the head; whereby attaching the tool to a fixture or fastener and turning the handle causes the head to rotate and move the bumps over the movable ramps to break or deform said ramp, thereby setting a torque limit.

DRAWINGS

The above-mentioned features of the present disclosure will become more apparent with reference to the following description taken in conjunction with the accompanying drawings wherein like reference numerals denote like elements and in which.

Figure 1:
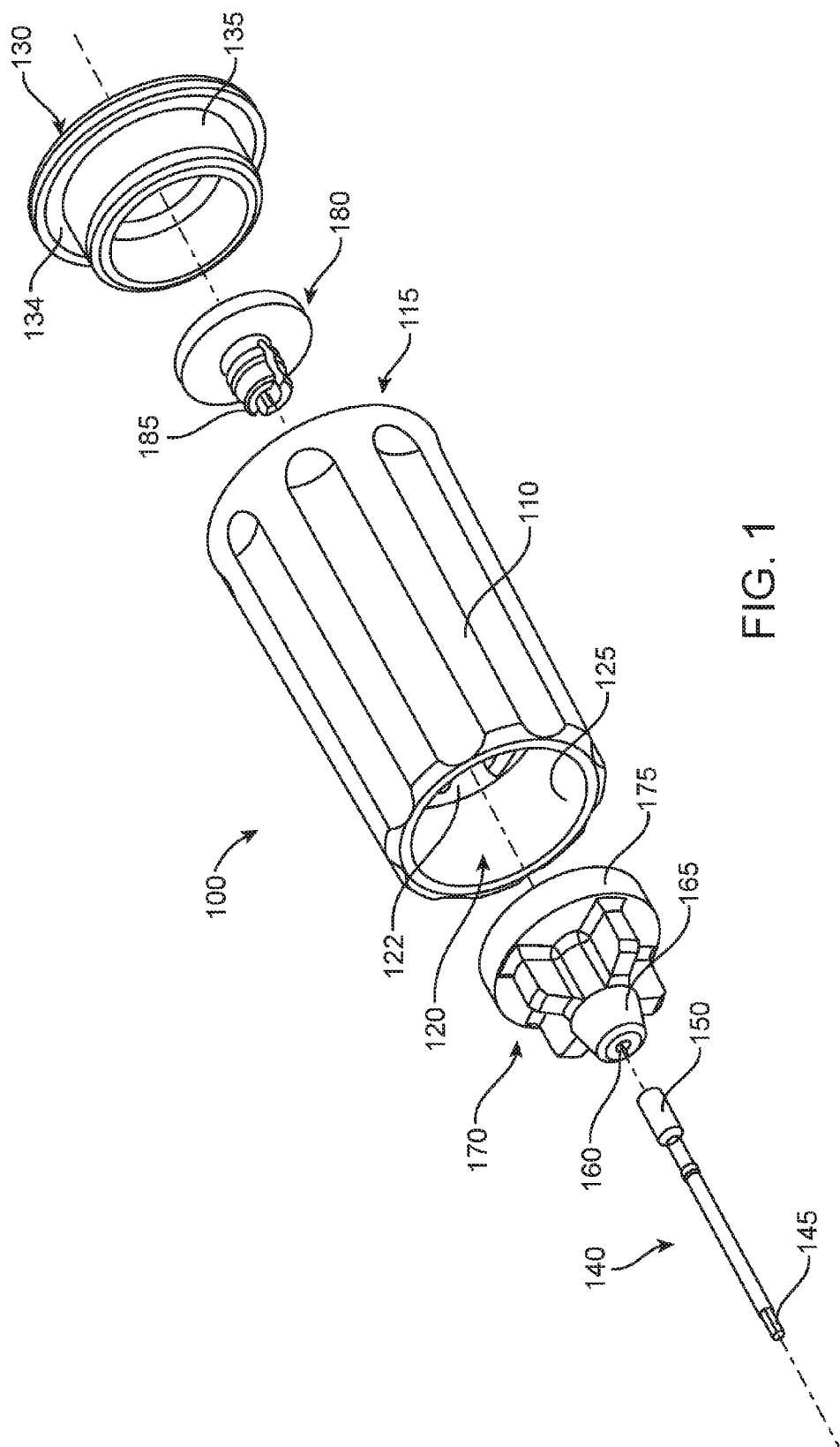
FIG. 1 shows a front perspective component view of some aspects of an exemplary implementation of a multiple use torque limiting device.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

Referring to FIGS. 1-4. In FIG. 1 there is shown an assembly view of a multiple use torque-limiting driver 100. The torque-limiting driver 100 has a generally hollow body 110 forming a handle with an open proximal end 115 an open distal end 120 and an internal circular wall 122 bisecting the handle into a front section 125 and a back section.

A circular cap 130 with a backside 132 a front side 134 and an annular wall 135 which extends from said front side 134 and of a size and shape to form a latch with said open proximal end 115.

A tool 140 with a tip 145 at its distal end and a fixed mount 150 at its proximal end is affixed at its proximal end into a mounting guide 160 located in the nose 165 which is extended from the front side of the head 170 component. The head component 170 is a support element. The head component is a movable circular element with an annular wall 175 formed opposite said nose on the backside. The annular wall defines a diameter around the circular head that fits within said open distal end 120.

Figure 2:
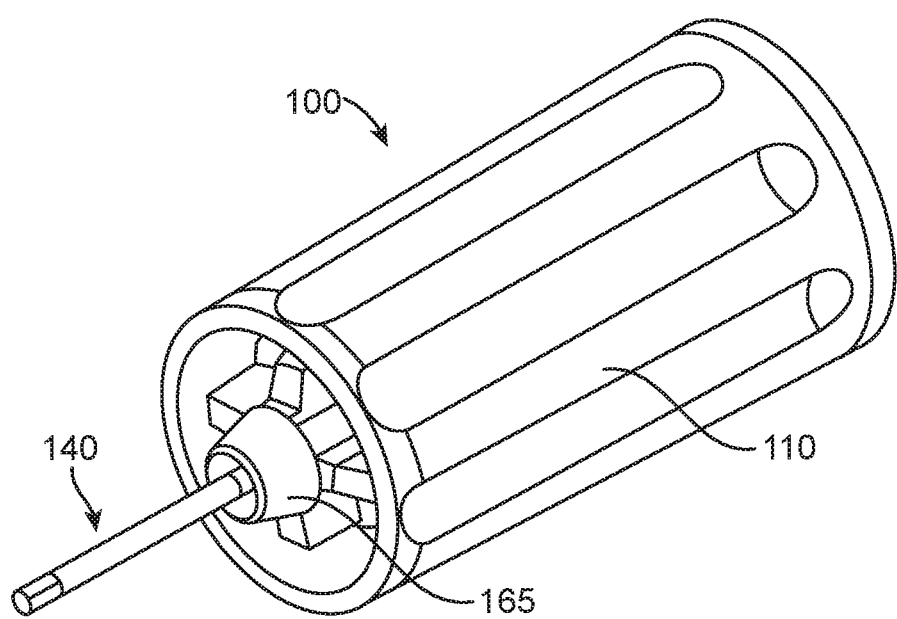
FIG. 2 shows a front perspective view of some aspects of an exemplary implementation of a multiple use torque limiting device.
Figure 3A:
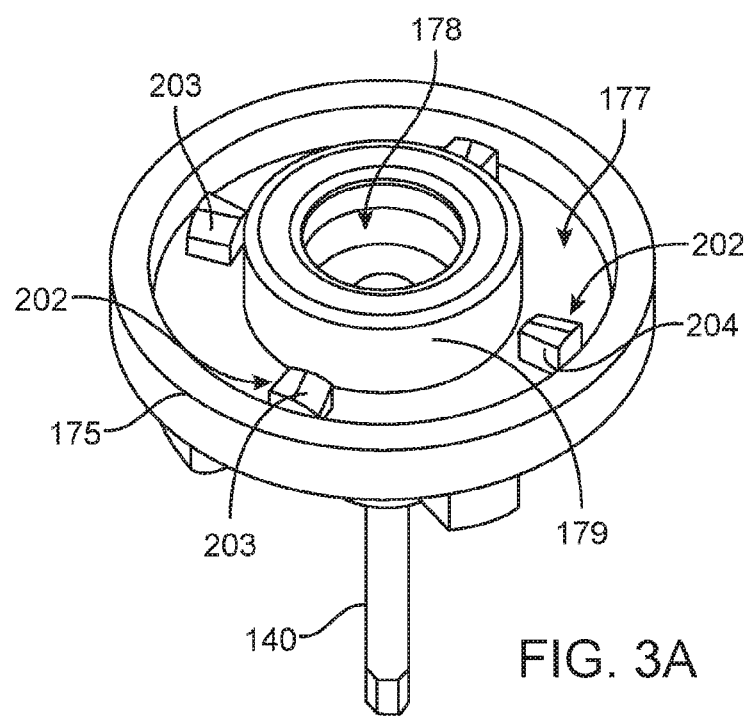
FIG. 3A shows a back view of the head component of FIGS. 1 and 2.
Figure 3B:
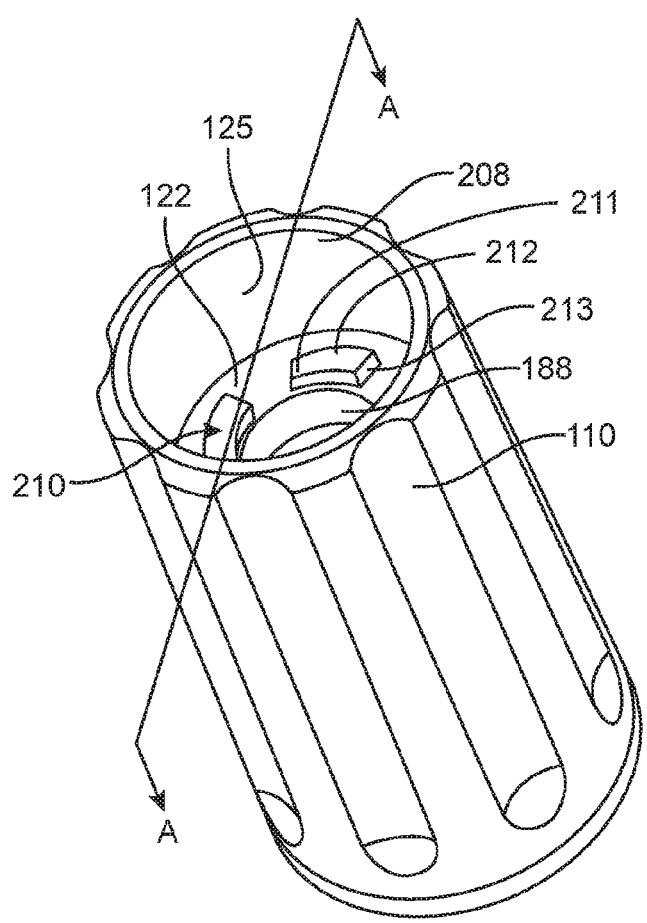
FIG. 3B shows a view of the front section of the of the handle component of FIGS. 1 and 2.
Figure 3C:
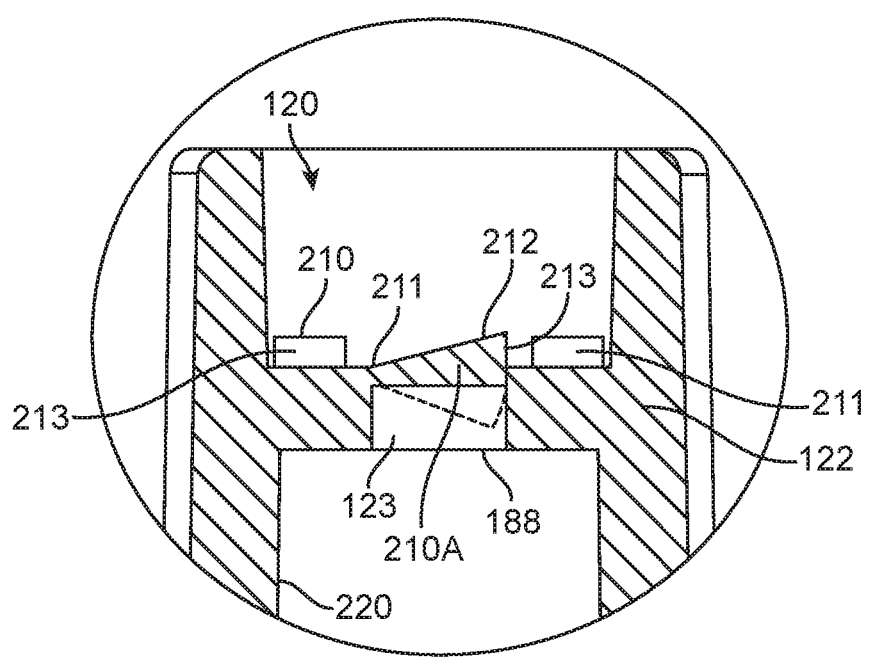
FIG. 3C show a sectional view along line "A"-"A" of FIG. 3B.
Figure 4:
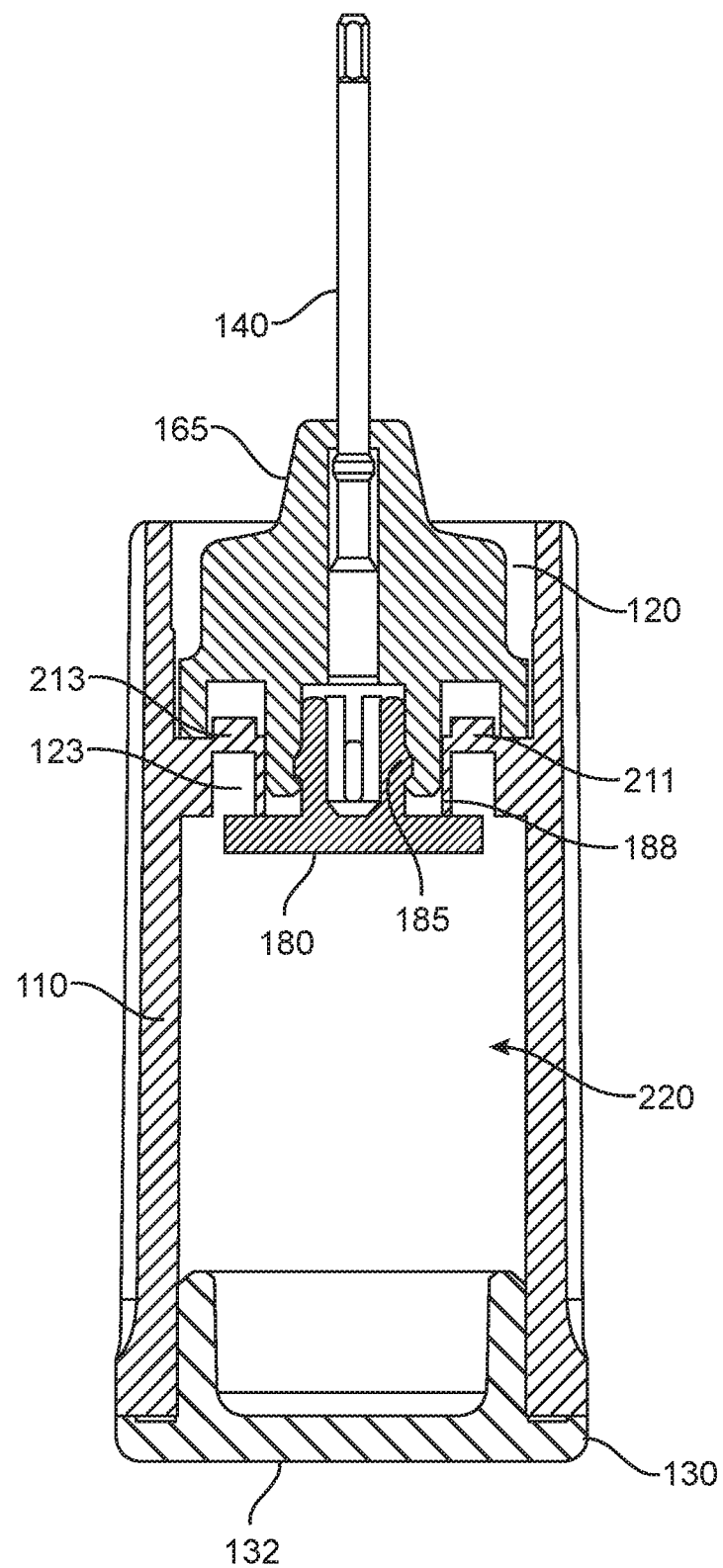
FIG. 4 shows a cut-away side view of some aspects of an exemplarily implementation of a multiple use torque limiting device.

Although not fully visible in FIGS. 1 and 2, said head component 170 supports a catch formed on its backside wherein a head plug 180 which provides a latch 185 that fits through a plug channel through internal circular wall 122. In FIGS. 3B and 4, the plug channel 188 is shown.

The back side 177 of the head 170 is surrounded by said annular wall 175. The plug catch 178, formed in a cylindrical peg 179 provides a point whereby said head plug can movably attach said head to the internal circular wall 122 whereon the support component may be rotated in furtherance of the disclosure. To effectuate a torque limited rotations as well as fixed reverse rotations (without torque limiting) a cooperative system is disclosed whereby a head piece attached to the bisecting internal circular wall via a head plug interacts with operational features formed on said internal wall 122. One or more bump stops 202 extend from, and are supported by, the back side 177 of the head component 170. Said stops 202, have an angled face 203 and a flat substantial flat jam 204 which is perpendicular to said backside 177. Upon rotation of said handle 110 when said tip 145 is engaged with a fastener, features of the internal circular wall and the head working cooperatively come into play.

Specifically, each bump stop 202 is a predetermined height and length with a pre-determined angled face 203 whereby, in conjunction with one or more lock torque ramps 210, together impart a predetermined amount of torque to said tip 145 for a predetermined number of passes (clicks) of bump stop(s) 202 over lock torque ramp(s) 210. The predetermined amount of force is also called an actuation force.

Each lock torque ramp is a movable flap molded to have certain properties. Said properties are determined by material, thickness, length of ramp and actuator. In the implementations disclosed herein, the actuators are bump stops formed on said face.

Each lock torque ramp has a body 210A. The lock torque ramp acts as a spring, extension of the internal wall, formed of the plastic the internal wall is formed of. The lock torque ramp(s) extend from the internal wall 122 via a first end 211. Each ramp has an elongated body 210A with a second end 212. Each ramp, at rest, is substantially above the internal wall extending into the front section 125. In use, the ramp body generally pivots about the first end 211, and moves generally axially into an opening 123 in the circular wall 122 beneath the ramp. The ramp body is displaced downward, into the opening 123, when adequate force from the bump stop 202 is applied to the ramp body as the bump stop 202 passes over the lock torque ramp. When the force is removed the ramp 210 returns upward, via spring action of the living hinge formed by the first end's connection with the internal wall, to the raised at rest position. The material the internal wall and ramp are formed of must provide the living hinge spring action whereby the ramp which will return to substantially it's original at rest position from before the application of force.

In operation, The angled face 203 of a bump stop makes contact with the first end 211 of said lock torque ramp and presses the movable lock torque ramp downward (into the space 123 in the internal wall 123)—said movement downward requires a pre-determined amount of force thereby establishing a torque limit for said driver. The plastic lock torque ramp will have some memory and spring upward after a bump stop passes there over. When the number of passes of bump stops over a ramp exceeds a life cycle or limit which the memory of the material forming the living hinge has the ramp, at its first end 211 connection to the internal wall, the force required to displace the ramp will be less than the required actuation force. In some instances when the life cycle limit has been met or exceeded the rest position of the ramps will be substantially at or below the internal wall. The memory of the movable ramps before the life cycle is exceeded is at rest in the extended or upward position. When the bump stop encounters the moveable ramp it may be used to apply pressure as it moves along the ramp, as the bump stop 202 moves up the ramp, the bump stop applies force to the movable ramp thereby moving said ramp downward relative to the bump stop. By angling said bump stop a smooth engagement of said ramp is achieved. Those of ordinary skill in the art will recognize that while an angle may achieve a smoother movement it is not a general limitation of the disclosure.

Each bump has a substantial flat jam 204 on one side which is perpendicular to said backside 177. During rotation in the selected direction of operation (shown in the figures as clockwise—but those of ordinary skill in the art will recognize that is could just as well be counterclockwise and it would still be within the scope of this disclosure), said head is held in close proximity to said bump stop(s) 202, in the reverse direction said substantially flat jam 204 encounter the leading edge 213 of said lock torque ramp and will drive the tool in reverse when said handle 110 is rotated.

FIG. 4 illustrates a cut-away assembled view of a multiple use torque limiting device with reversible features. Head plug 180 via its extended latch 185 fits through the plug channel 188 of the internal circular wall 122 and mates with, to be held in, the plug catch 178 of said head. In this view, the lock torque ramps 210 and the opening 123 into which they move (when under force) ramp are visible. Behind the internal circular wall 122 is the back section 220 wherein fits the cap 130. The internal wall which bisected the body 110 demarcates the boundary between a first section 125 (which is also the front section) and a second section 220 (which is also the back section).

Figure 5A:
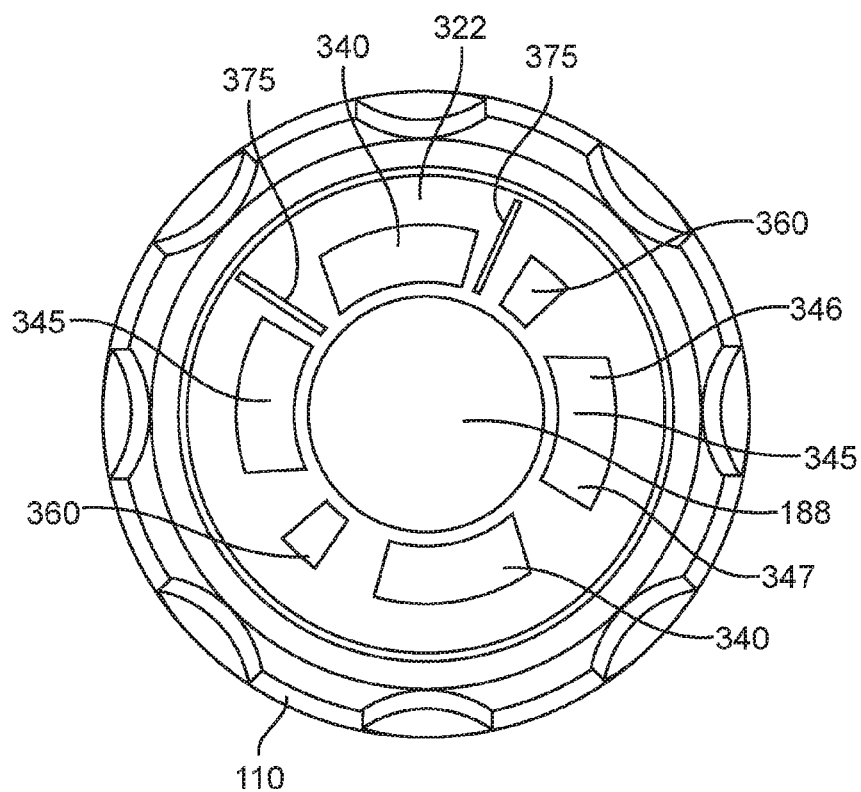
FIGS. 5A and 5B show features of an exemplary implementation with offset ramps and ribs.
Figure 5B:
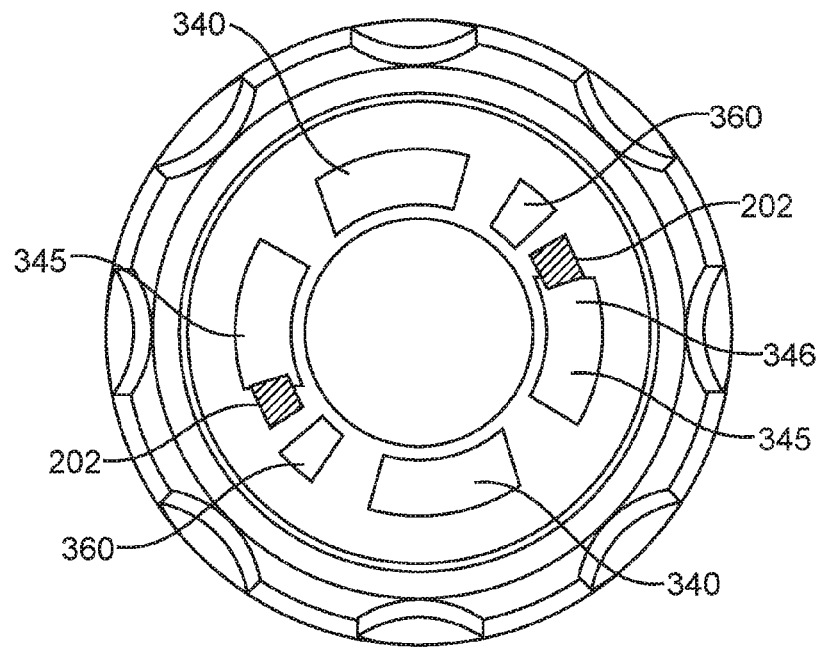

FIGS. 5A and 5B illustrate exemplary implementations of several aspects of a multiple use torque limiting device. In this implementation the internal wall 322 bisecting the hollow body 110 replaces the internal wall illustrated in FIGS. 1-4. Said internal wall 322 supports pairs of lock torque ramps 340 and 345. Said pairs of ramps are offset by 180 degrees. However, the pairs are offset from the other pair by less than 90 degrees. Also indicated are hard stops 360 and click ribs 375. Click ribs provide a positive feel or sound which indicates a bump stop 202 has passed over said click rib. Hard stops provide a stiff object whereby said bump stop, in a reverse direction, can be used to reverse spin a tool affixed to a driver such as those described in reference to FIGS. 1-4. Those of ordinary skill in the art will recognize that the ramps may be individual and not pairs and that pairs are not a limitation and depending on variables such as the amount of torque to be limited and the smoothness of operation desired.

FIG. 5B is an overlay view of bump stops 202 on the backs side of a nose element at the first end 346 of torque ramps 345. In this implementation two bump stops offset by 180 degrees are utilized. The first end being affixed to said internal wall 322. During a torque limited stroke, said bump stops 202 pass from the first end 346 of the ramps to the second end 347. The second end is a free end which is raised in its unused state. Preferably the second end of said ramp is frangible; it will be deformed and broken after one passage of said bump stop 202 thereover and will no longer be raised up to interact with the bump stops 202. It is acceptable if said second end has some memory and comes back up after said bump stop passes thereover. For such instances wherein said second end 347 may rise upward after a stroke, the bump stop 202 may be constructed with an angled face in the reverse direction whereby said bump stop can pass backwards over said second end without catching said second end but rather will pass to said hard stop to apply reverse force to a tool.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A disposable torque limiting device comprising:
    a hollow body with an open proximal end and an open distal end forming a handle, said hollow body further comprising an internal wall dividing said hollow body into a front section and a back section, at least one torque limiting movable ramp integrally formed on a front side of the internal wall; the torque limiting movable ramp pivotally connected to the internal wall via a living hinge and having an elongated ramp body projecting at an incline away from the internal wall;
    a channel hole formed through said internal wall fluidly connecting said front section and said back section;
    a head having a front side with a nose extended therefrom which has a tool mounted therein;
    said head having an annular back side surface located between an outermost annular wall sized to movably fit inside the front section of the hollow body and an innermost cylindrical peg wall, the innermost cylindrical peg wall having a catch feature formed thereon, the annular back side surface containing at least one bump stop protruding therefrom;
    a plug having a base sized to fit inside the back section of the hollow body but sized to be larger than the channel hole, the plug having an extended latch protruding from the base that is sized and shaped to fit through the channel hole and fasten to the catch feature on the innermost cylindrical peg wall to secure the tool and the head in the front section;
    whereby when the handle is twisted relative to the tool, the at least one torque limiting movable ramp on the hollow body will rotate toward the at least one bump stop on the head to an engagement point where the bump stop contacts the at least one torque limiting movable ramp, at the engagement point, additional twisting of the handle will result in a twisting of the tool with a torque limited at level where the at least one bump stop pivotally deflects the elongated ramp body toward the internal wall allowing the bump stop to rotate past the at least one generally torque limiting movable ramp.

2. The device of claim 1, wherein the at least one torque limiting movable ramp is constructed out of a plastic material with memory.

3. The device of claim 2 wherein the least one torque limiting movable ramp will return to its inclined position after the bump stop pivotally deflects the elongated ramp body toward the internal wall via spring action of the plastic material with memory.

4. The device of claim 3 wherein the least one torque limiting movable ramp requires an application of a predetermined actuation force to cause the elongated ramp body to pivotally deflect.

5. The device of claim 4 wherein when a life cycle limit of the living hinge is exceeded the elongated ramp body will become displaced by the application of less than the actuation force.

6. The device of claim 5 wherein when a life cycle limit of the living hinge is exceeded the elongated ramp body may no longer return to its inclined position away from the internal wall.

7. A torque limiting system comprising:
    a hollow body divided by an internal wall into a front section and a back section;
    at least one torque limiting movable ramp integrally formed on a front side of the internal wall; the torque limiting movable ramp pivotally connected to the internal wall via a living hinge and having an elongated ramp body projecting at an incline away from the internal wall;
    a channel hole formed through said internal wall fluidly connecting said front section and said back section;
    a head having a front side with a nose extended therefrom which has a tool mounted therein;
    said head having an annular back side surface located between an outermost annular wall sized to movably fit inside the front section of the hollow body and an innermost cylindrical peg wall, the innermost cylindrical peg wall having a catch feature formed thereon, the annular back side surface containing at least one bump stop protruding therefrom;
    a plug having a base sized to fit inside the back section of the hollow body but sized to be larger than the channel hole, the plug having an extended latch protruding from the base that is sized and shaped to fit through the channel hole and fasten to the catch feature on the innermost cylindrical peg wall to secure the tool and the head in the front section;
    whereby when the handle is twisted relative to the tool, the at least one torque limiting movable ramp on the hollow body will rotate toward the at least one bump stop on the head to an engagement point where the bump stop contacts the at least one torque limiting movable ramp, at the engagement point, additional twisting of the handle will result in a twisting of the tool with a torque limited at level where the at least one bump stop pivotally deflects the elongated ramp body toward the internal wall allowing the bump stop to rotate past the at least one generally torque limiting movable ramp.

8. The device of claim 7 wherein the at least one torque limiting movable ramp is integral to the internal wall and is constructed out of a plastic material with memory.

9. The device of claim 8 wherein the least one torque limiting movable ramp will return to its inclined position after the bump stop pivotally deflects the elongated ramp body toward the internal wall via spring action of the plastic material with memory.

10. The device of claim 9 wherein the least one torque limiting movable ramp requires an application of a predetermined actuation force to cause the elongated ramp body to pivot pivotally deflect.

11. The device of claim 10 wherein when a life cycle limit of the living hinge is exceeded the elongated ramp body will become displaced by the application of less than the actuation force.

12. The device of claim 11 wherein when a life cycle limit of the living hinge is exceeded the elongated ramp body may no longer return to its inclined position away from the internal wall.

* * * * *